United States Patent [19]

Mesek

[11] Patent Number: 4,960,477
[45] Date of Patent: Oct. 2, 1990

[54] DISPOSABLE DIAPER WITH FOLDED ABSORBENT BATT

[75] Inventor: Frederick K. Mesek, San Diego, Calif.

[73] Assignee: McNeil-PPC, Inc., Milltown, N.J.

[21] Appl. No.: 302,038

[22] Filed: Jan. 24, 1989

Related U.S. Application Data

[60] Continuation of Ser. No. 28,411, Mar. 18, 1987, abandoned, which is a division of Ser. No. 726,040, Apr. 22, 1985, Pat. No. 4,670,011, which is a continuation-in-part of Ser. No. 557,190, Dec. 1, 1983, abandoned.

[51] Int. Cl.⁵ .............................................. B32B 7/00
[52] U.S. Cl. ................................. 156/209; 156/220; 156/276; 604/378; 604/379
[58] Field of Search ............... 156/70, 145, 179, 202, 156/204, 209, 219, 220, 221, 222, 223, 226, 276; 604/304, 308, 380, 378, 379, 389 R, 389 A, 283, 368, 369; 428/283, 286, 301, 302, 327

[56] References Cited

U.S. PATENT DOCUMENTS

| | | |
|---|---|---|
| 2,644,454 | 7/1953 | Morhard . |
| 3,017,304 | 1/1962 | Burgeni .............................. 156/281 |
| 3,344,789 | 10/1967 | Arnold et al. . |
| 3,381,688 | 5/1968 | Satas . |
| 3,612,055 | 10/1971 | Mesek . |
| 3,670,731 | 6/1972 | Harmon . |
| 3,768,480 | 10/1973 | Mesek et al. . |
| 3,888,257 | 6/1975 | Cook et al. . |
| 3,903,889 | 9/1975 | Torr . |
| 3,938,522 | 2/1976 | Repke . |
| 3,965,904 | 6/1976 | Mesek et al. . |
| 4,055,184 | 10/1977 | Karami . |
| 4,079,739 | 3/1978 | Whitehead . |
| 4,102,340 | 7/1978 | Mesek et al. . |
| 4,105,033 | 8/1978 | Chatterjee et al. . |
| 4,145,464 | 3/1979 | McConnell et al. ................. 604/378 |
| 4,186,165 | 1/1980 | Aberson et al. . |
| 4,232,674 | 11/1980 | Melican .............................. 604/370 |
| 4,251,643 | 2/1981 | Harada et al. . |
| 4,269,188 | 5/1981 | Nishizawa et al. . |
| 4,327,728 | 5/1982 | Elias . |
| 4,333,463 | 6/1982 | Holtman . |
| 4,364,992 | 12/1982 | Ito et al. . |
| 4,372,312 | 2/1983 | Fendler et al. . |
| 4,381,782 | 5/1983 | Mazurak et al. ..................... 604/378 |
| 4,381,783 | 5/1983 | Elias ..................................... 604/378 |
| 4,389,211 | 6/1983 | Lenaghan ........................... 604/383 |
| 4,410,324 | 10/1983 | Sabee ............................... 604/385 R |
| 4,411,660 | 10/1983 | Dawn et al. ....................... 604/378 |
| 4,425,127 | 1/1984 | Suzuki et al. ...................... 604/369 |
| 4,461,621 | 7/1984 | Karami et al. ..................... 428/286 |
| 4,500,316 | 2/1985 | Damico ............................ 604/385 R |
| 4,518,451 | 5/1985 | Luceri et al. ....................... 156/221 |
| 4,519,800 | 5/1985 | Merry ............................... 604/385 A |
| 4,576,596 | 3/1986 | Jackson et al. .................... 604/380 |

FOREIGN PATENT DOCUMENTS

| | | |
|---|---|---|
| 489308 | 11/1927 | Fed. Rep. of Germany . |
| 2402594 | 4/1979 | France . |
| 147113 | 4/1977 | Japan . |
| 01455 | 7/1980 | World Int. Prop. O. . |

Primary Examiner—Michael W. Ball
Assistant Examiner—Louis Falasco
Attorney, Agent, or Firm—Lawrence D. Schuler

[57] ABSTRACT

An improved absorbent unit for a disposable diaper, or the like, wherein a fibrous batt is initially generally rectangularly shaped, and is cut so as to define side flaps which are folded over into overlapping relationship with one another in the central portion of the batt to define a multiple layer crotch region for increased liquid storage capacity. The batt is provided with a thickened densified skin at one side thereof for increased strength and stability, and for transporting liquid into remote areas of the batt. In a further embodiment, a quantity of highly liquid-sorbent superabsorbent material is provided in discrete spaced-apart regions between upper and lower fibrous webs of the diaper batt, with a network of densified wicking embossments and at least one integral densified wicking layer provided for promoting efficient wicking and transport of liquid within the absorbent structure.

26 Claims, 4 Drawing Sheets

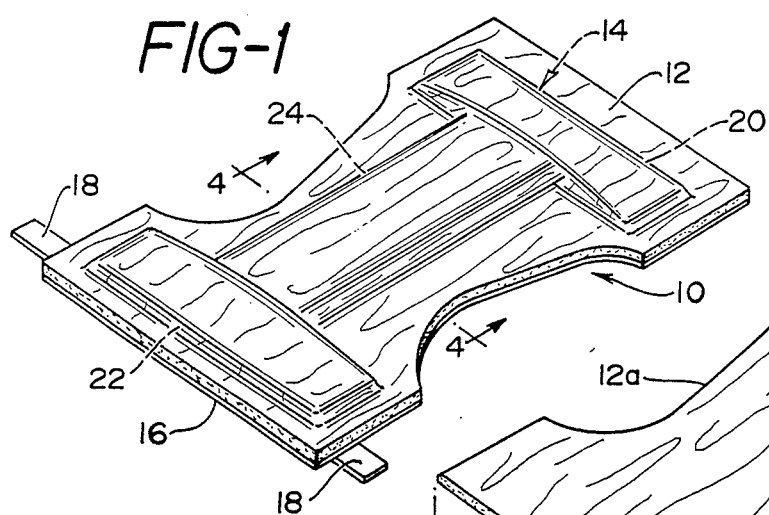
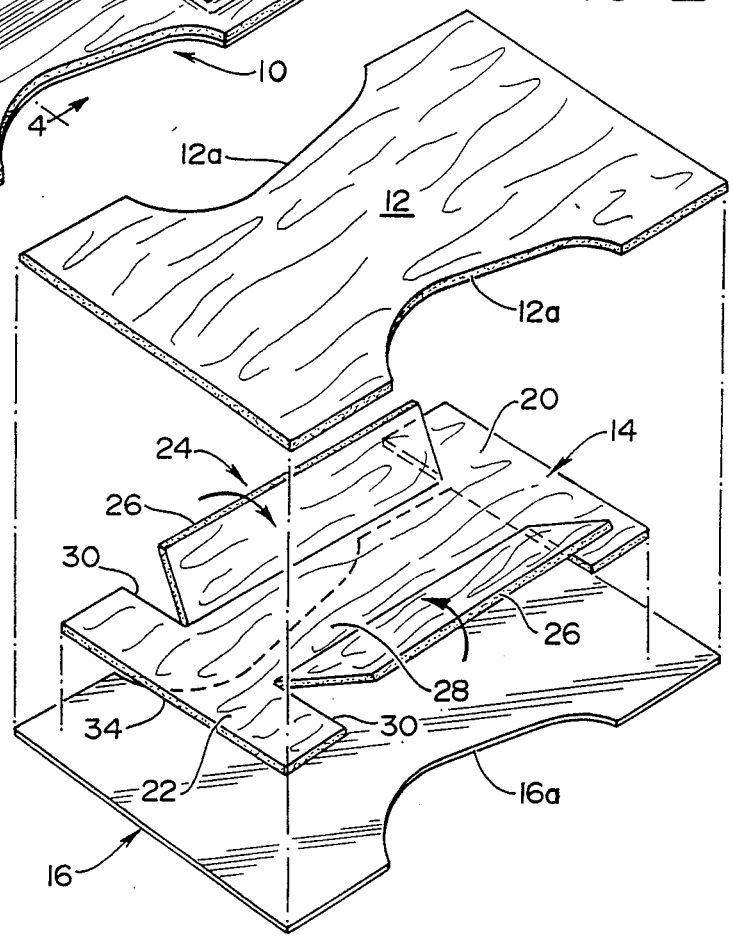
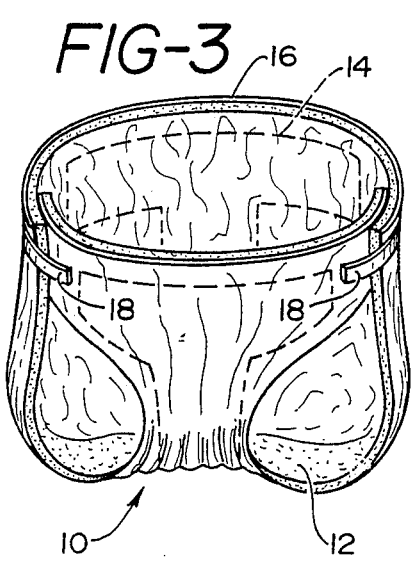
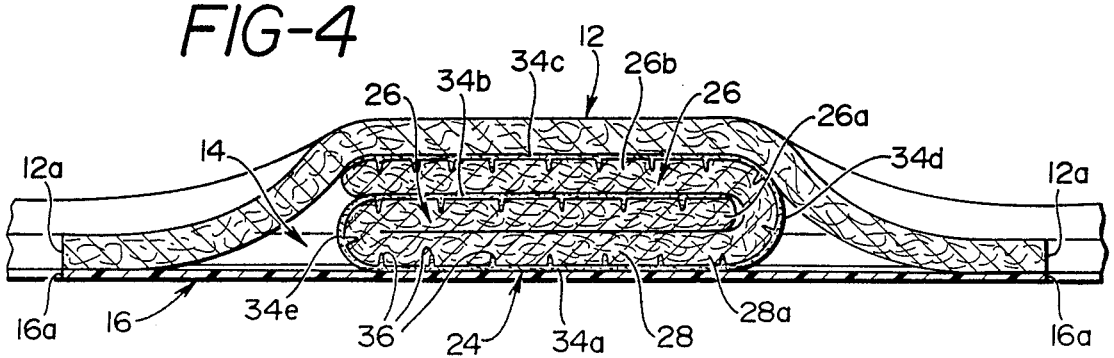

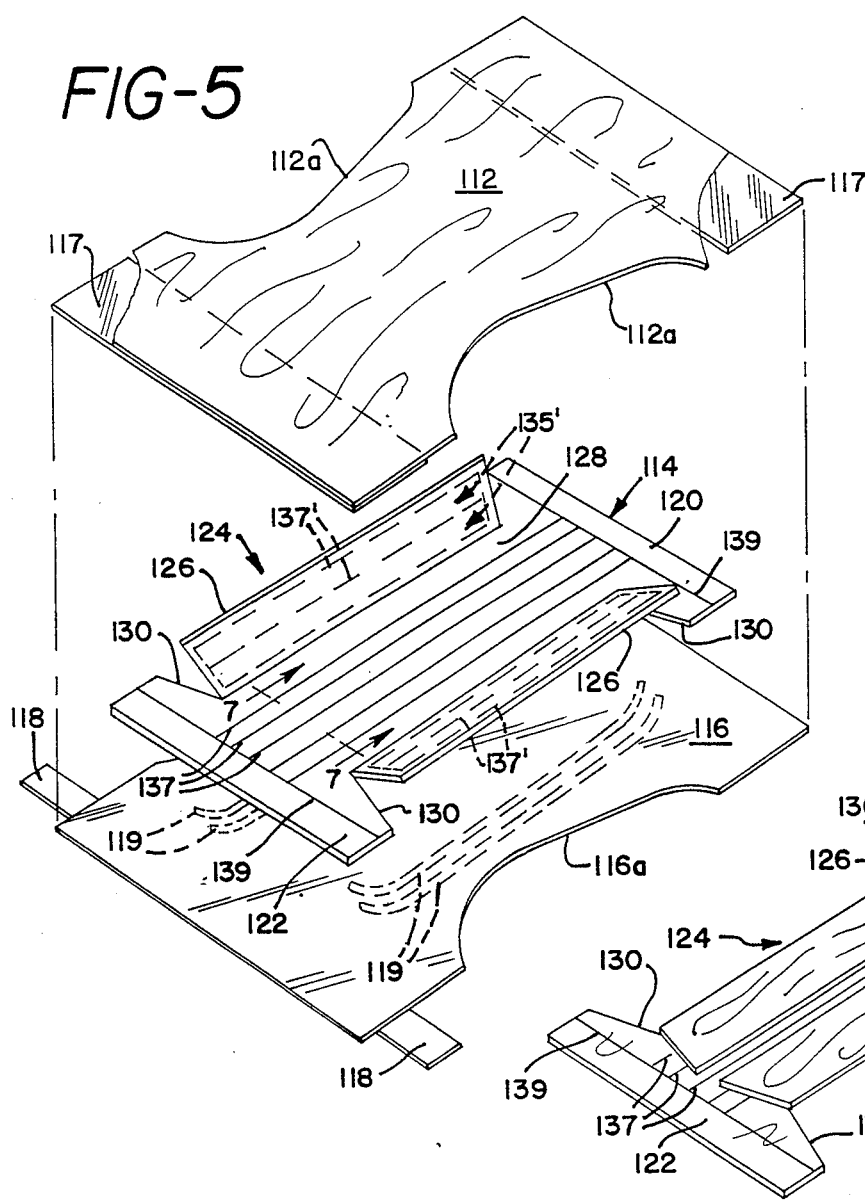

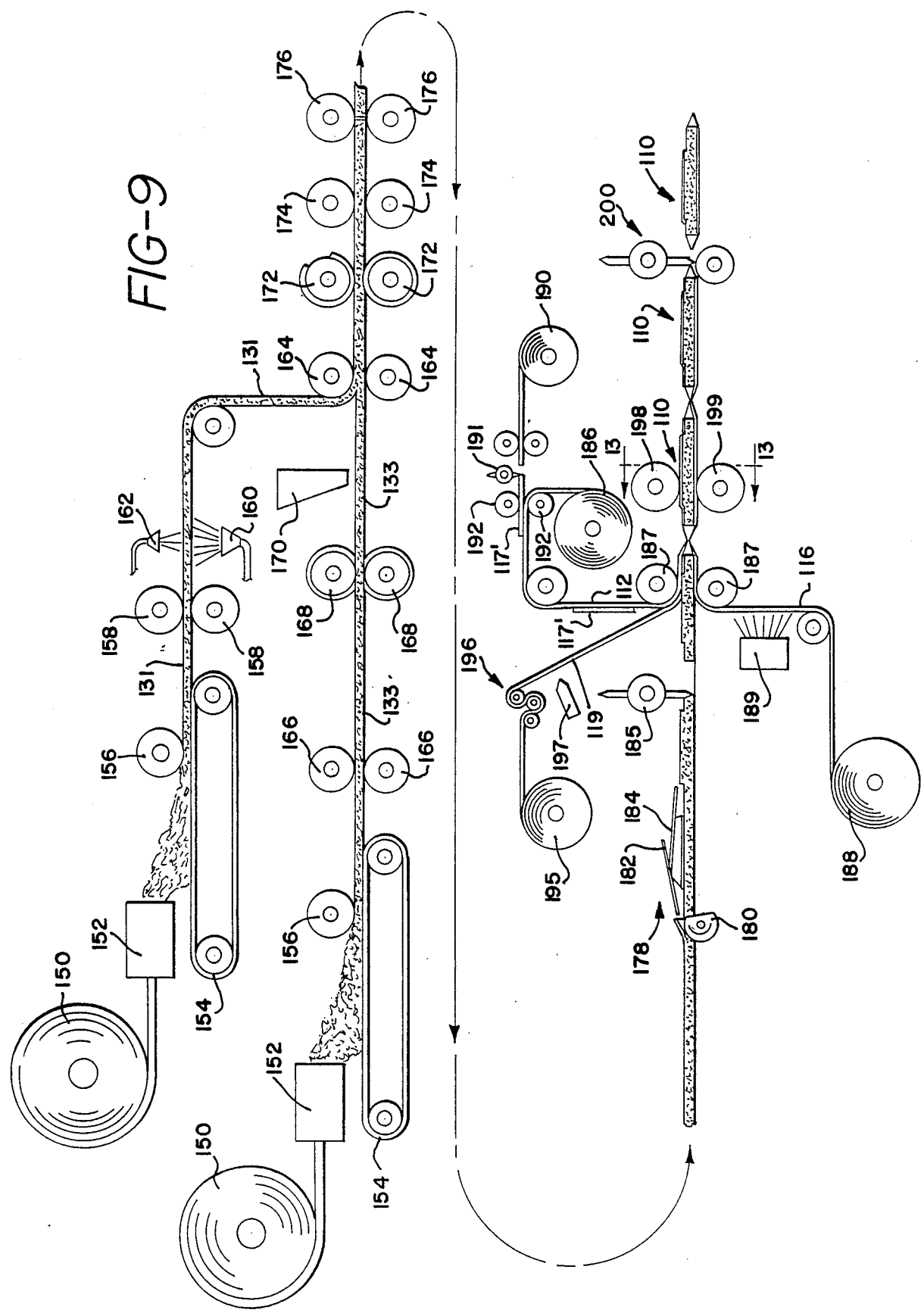

DISPOSABLE DIAPER WITH FOLDED ABSORBENT BATT

This application is a continuation of application Ser. No. 07/028,411, filed 3/18/87 abandoned, which is a division of Ser. No. 06/726,140 filed Apr. 23, 1985, Pat. No. 4,670,011 which is a continuation-in-part of Ser. No. 06/557,190 filed Dec. 1, 1983 abandoned.

TECHNICAL FIELD OF THE INVENTION

This invention relates to absorbent structures for absorbent articles such as disposable diapers. More particularly, this invention relates to disposable diapers including a batt which is constructed and arranged to provide increased strength and absorptive capacity in the crotch region of the diaper, while at the same time providing an improved wicking mechanism for transporting liquid away from an initially wetted area into remote regions of the batt. Embodiments of the diaper including highly liquid-sorbent superabsorbent material are also disclosed wherein the absorbent unit or structure thereof is configured to promote liquid wicking or transport within the fibrous matrix of the structure to optimize utilization of the absorptive capacity of the superabsorbent material while maintaining the stability and structural integrity of the absorbent structure.

BACKGROUND OF THE INVENTION

Disposable diapers provide substantial advantages and convenience over diapers intended to be laundered and reused, and in recent years disposable diapers have met with increased success in the marketplace. Typical disposable diaper structures include a moisture retaining layer of relatively high liquid holding capacity sandwiched between a moisture pervious facing layer to be directed against the infant's skin, and a moisture impervious plastic backing sheet to confine moisture within the moisture retaining layer. Such diapers are shown in U.S. Pat. No. 3,612,055 to Mesek et al. and in U.S. Pat. No. Re: 26,151 to Duncan et al.

The moisture retaining layer of prior art diapers have typically been comprised of a batt of loosely compacted cellulosic fibers. It has been known to provide such absorbent batts with an integrally formed densified paper-like layer or skin, and U.S. Pat. Nos. 3,017,304 to Burgeni and 3,612,055 to Mesek et al. are typical of such constructions. It is also known to provide absorbent batts having a continuous densified paper-like layer or skin with longitudinally extending thickened densified regions for directing moisture in a lengthwise direction of the batt, and Repke U.S. Pat. No. 3,938,522 is typical of such constructions.

It is also known to provide disposable diapers with reduced width crotch regions to reduce the bulk and provide improved fit and comfort. Such diapers are generally I-shaped, T-shaped or hour glass-shaped, and U.S. Pat. Nos. 3,559,648 to Mason, Jr. and 3,768,479 to Widland are typical of such constructions.

It is also known to provide absorbent batts for disposable diapers with increased liquid holding capacity in the central region of the batt, and heretofore this has been done by providing an extra batt layer (U.S. Pat. No. 3,612,055), depositing more absorbent material in the mid-portion of the batt (U.S. Pat. No. 3,938,522), or folding over the side marginal edges of the batt (U.S. Pat. No. 3,559,648). Such absorbent batts have had inadequate inherent structural integrity, and have not provided an adequate wicking mechanism for directing liquid away from an initially wetted area.

The use of so-called superabsorbent hydrocolloid materials in absorbent articles is also known for enhancing the absorbent capacity thereof. Materials of this nature are highly liquid-sorbent, and are capable of absorbing and retaining many times their own weight in liquid. While such materials are highly absorbent, incorporation of such materials in an absorbent article, such as a disposable diaper, can be problematic. Specifically, such superabsorbent materials generally do not act to efficiently wick or transport liquid, and thus, an associated wicking mechanism should be provided for promoting wicking of liquid throughout an absorbent product. In practice, such superabsorbent materials can actually prevent liquid-wicking, in that such materials can tend to coalesce and form a gelatinous mass when wetted which prevents wicking of liquid to unwetted portions of the material. This phenomenon is commonly referred to as "gel blocking", and can undesirably act to prevent effective and efficient use of the superabsorbent material by isolating liquid from unwetted portions of the material. While blends of particulate superabsorbent material and fibrous material such as wood pulp have been employed for enhancing absorptive capacity of an article (such as in U.S. Pat. No. 4,186,165, to Aberson et al.), it is believed that blending the absorptive materials in this manner can act to diminish the absorptive capacity of the fibrous material, since the superabsorbent swells and fills the void volumes of the fibrous material, which otherwise provide the liquid-holding capacity of the material. Poor wicking of liquid is also a problem in such superabsorbent/fibrous blends.

Furthermore, the very substantial swelling which takes place when such superabsorbent material absorbs liquid can undesirably impair the structural integrity or stability of an absorbent product into which such material is incorporated. Abating degradation of the structural integrity of an absorbent article having superabsorbent is particularly important since the article can be subjected to continued use after wetting (such as the case of a disposable diaper) with such integrity also facilitating handling and disposal of the article after use. Additionally, the texture of some superabsorbent materials after wetting can be objectionable, thus making it further desirable for the structural integrity of an absorbent article to be maintained after use so that the wetted superabsorbent is held in position within the article after use.

One manner in which superabsorbent material has been incorporated in an absorbent article is shown in U.S. Pat. No. 4,232,674, to Melican. This patent discloses deposition of superabsorbent material in a predetermined pattern, such as comprising parallel stripes, sandwiched between two layers of relatively non-absorbent tissue paper. The patent states that providing the pattern of superabsorbent in the form of stripes leaves channels between the stripes along and within which liquid can flow. While flow is stated as being primarily capillary to start with, larger channels are defined as the superabsorbent material swells, which diminishes flow caused by capillary action, since such capillary flow is promoted by close spacing of fibers of a fibrous material. It is further believed that this type of absorbent structure does not lend itself to maintaining the stability or structural integrity thereof attendant to swelling of the superabsorbent since it is specifically contemplated that the non-absorbent layers between which the superabsorbent is deposited are intended to be moved apart and separated during swelling of the superabsorbent. Further, it is believed that providing superabsorbent material between two tissue layers, in accordance with the teachings of this patent, does not address problems associated with the relatively large liquid volumes which must be absorbed and retained quickly by a disposable diaper. It is noted that this patent only discloses the embodiments of the tissue/superabsorbent construction in a sanitary napkin and tampon which generally need only absorb relatively small volumes of liquid at relatively small flow rates when compared to the desired characteristics of a disposable diaper.

U.S. Pat. No. 4,461,621, to Karami et al, also discloses an absorbent article which incorporates superabsorbent material. The article includes a backing sheet of fluid impervious material, and a fluid pervious cover sheet. A first absorbent pad comprising a loosely formed fibrous mass is provided adjacent the cover sheet, with either the upper or lower surface of the first pad coated with an absorbent polymer material. The article has a separate second absorbent pad intermediate the first pad and the backing sheet comprising a mass of fibers having a compressed region extending throughout a substantial part of the second pad. The polymer coating is described as extending at least a substantial part of the width of the pad and from the third to the sixth tenth of the length of the pad. The patent discloses providing the polymer coating in two strips with a space therebetween to eliminate "gel block" at the central point of fluid excretion. As in other constructions, it is believed that the arrangement disclosed in this patent does not lend itself to maintaining the stability or structural integrity of the absorbent structure attendant to absorption and swelling of the polymer material, particularly when the polymer material is positioned on the surface of the first absorbent pad adjacent the second pad.

It would therefore be desirable to provide an absorbent unit for a disposable diaper, or the like, with increased liquid storage capacity in the central region thereof, while providing a wicking layer directly adjacent to the undersurface of the facing layer in contact with the infant's skin for rapidly directing liquid away from an initially wetted area. It would also be desirable to provide such a batt with a wicking mechanism whereby liquid spreading outwardly would be directed downwardly into lower portions of the batt remote from the layer in contact with the infant's skin. It would also be desirable to provide the mid-portion of such a batt with a strengthening means, so as to provide increased structural integrity, particularly when the diaper is to be worn for a prolonged period of time, such as overnight.

It would also be desirable to provide a disposable diaper having an absorbent unit incorporating highly liquid-sorbent superabsorbent material for enhanced liquid-holding capacity. Such a diaper should preferably be configured to promote wicking of liquid to all of the superabsorbent material provided therein, thus providing a high rate of liquid absorbency as is important in a disposable diaper.

SUMMARY OF THE INVENTION

The present invention provides an improved absorbent unit for a disposable diaper or the like wherein the body or central portion of the batt is defined by multiple batt thicknesses for increased liquid holding capacity. In accordance with one aspect of the invention, the batt is provided with an integrally formed, densified paper-like skin that is positioned adjacent to the undersurface of the facing layer that is to contact the infant's skin, so as to provide a wicking mechanism for rapidly directing liquid away from an initially wetted area for absorption into remote regions of the batt. In accordance with another aspect of the present invention, a wicking mechanism extends downwardly from the upper portion of the batt for directing liquid downwardly toward the lower portion of the batt. In accordance with still another aspect of the present invention, a medial layer of the batt is provided with an integrally formed densified paper-like skin for increased strength and stability, as well as for improved liquid transport.

The batt of the present invention may be formed by cutting the longitudinal side edges of the batt to define side flaps which may be folded inwardly to provide multiple layers in the body or central portion of the batt. In a preferred embodiment of the invention the batt is cut about ⅓ of its width dimension so that the side flaps of the batt and the medial section thereof are of generally equal dimension. With this arrangement, the side flaps can be folded into overlapping relationship with one another to provide an absorbent unit with three layers in the central region thereof. The desired wicking arrangement, and increased strength, can be provided by forming such a batt with a continuous densified paper-like skin, or layer, on the undersurface thereof. It is most desired to associate a batt of the above-described type with a diaper product wherein the other diaper components (the facing and backing layers) are shaped, or contoured, for improved fit about the perineal region of an infant.

In a further embodiment of the present invention, a disposable diaper is disclosed having an improved absorbent unit or structure which incorporates highly liquid-sorbent superabsorbent material for significantly enhancing the liquid-holding capacity of the diaper. As in the previously described embodiment, this form of the present invention includes a highly porous, cellulosic fibrous batt, which is preferably provided with a generally I-shaped configuration formed from an initially generally rectangular member. The batt includes end portions and a central portion, wherein the central portion includes a medial section flanked by a flap section at each side thereof. Each flap section is folded into overlapping relation with the medial section so that the outer edges of the flap sections are positioned generally adjacent each other along the longitudinal centerline of the batt.

In this embodiment, the fibrous batt comprises first upper and second lower fibrous webs which are superposed to define a web interface therebetween. Significantly, the medial portion of the fibrous batt is provided with a quantity of highly liquid-sorbent, superabsorbent material which is positioned at the web interface, with the superabsorbent material being disposed in discrete, preferably longitudinally elongated spaced apart parallel regions. This configuration provides areas between the discrete regions of superabsorbent material which are relatively free of the superabsorbent material.

In order to promote wicking of liquid to various portions of the absorbent structure, the first and second webs of the fibrous batt are formed with relatively densified and compacted, liquid-wicking embossments in the superabsorbent-free areas adjacent the discrete regions of superabsorbent material. In the preferred form, these liquid-wicking embossments are provided in spaced apart parallel relation to each other between and on respective opposite sides of the longitudinally extending discrete regions of superabsorbent material. The provision of these wicking embossments not only provides a highly efficient wicking mechanism in intimate association with the regions of superabsorbent material for distribution of liquid to all of the superabsorbent, but further desirably acts to join the first and second webs to each other to provide the fibrous web batt with desired structural integrity and stability, even attendant to swelling of the wetted superabsorbent material.

For further enhancing the stability and wicking characteristics of the fibrous batt, it is preferred that at least the medial section of the batt include a paper-like, densified compacted cellulosic fibrous wicking layer formed integrally with one of the first and second webs. While this densified wicking layer can be formed on one of the outer surfaces of the first and second web, it is preferred that the wicking layer be provided at the interface of the two webs, thus positioning the wicking layer in intimate association with the discrete regions of superabsorbent material provided at the web interface. The formation of this densified wicking layer desirably provides a means for preventing splitting or like degradation of the fibrous batt attendant to swelling of the wetted superabsorbent material. Such stability-enhancing means can also be provided in the form of another paper-like densified compacted cellulosic fibrous wicking layer formed at the outer surface of one of the fibrous webs, or in the form of a paper tissue layer positioned at the interface of the webs above the superabsorbent material, positioned above the medial section of the batt beneath its flaps, or positioned above the fibrous batt structure beneath the diaper facing sheet.

In order to confine and retain the superabsorbent material in position within the fibrous batt, the batt can further be formed with densified compacted embossments which extend transversely of the parallel longitudinal embossments, generally at the ends of the longitudinal embossments and at the ends of the longitudinally extending discrete regions of superabsorbent material. By this construction, each discrete region of superabsorbent is essentially bounded or confined by the densified embossments formed in the first and second fibrous webs, further desirably enhancing the stability of the structure. Because of the desirably highly liquid-sorbent characteristics of the superabsorbent material, absorbency of the diaper can be further enhanced by providing each of the flap sections of the fibrous batt structure with at least one discrete region of the superabsorbent material, with each flap section including relatively densified liquid-wicking embossments bounding the discrete region of superabsorbent material therein.

A method of manufacturing a disposable diaper having discrete regions of superabsorbent is also disclosed. Manufacture is preferably effected by formation of the first and second fibrous webs of the structure, with deposition of a quantity of superabsorbent material on the second fibrous web effected on a medial section thereof to provide the desired plurality of spaced apart discrete regions of superabsorbent material. The first and second webs are then positioned in superposed relation such that the superabsorbent is positioned at the interface of the webs. The fibrous batt thus formed is cut to form a pair of flap sections at respective opposite sides of the medial section of the batt, with the flap sections folded at respective fold lines into overlapping relation with the medial section. Densified compacted wicking embossments are preferably formed between and adjacent to the discrete regions of superabsorbent material, with a densified compacted wicking layer further preferably integrally formed with one of the first and second fibrous webs.

Numerous other advantages and features of the present invention will become readily apparent from the following detailed description, the appended drawings, and the accompanying claims.

BRIEF DESCRIPTION OF THE DRAWINGS

FIG. 1 is a perspective view of a disposable diaper formed in accordance with the teachings of the present invention and laid out flat in preparation for application to an infant;

FIG. 2 is an exploded perspective view of the disposable diaper of FIG. 1, and illustrating the batt in an intermediate step of formation;

FIG. 3 is a perspective view of the diaper of the present invention as applied to an infant;

FIG. 4 is an enlarged cross-sectional view taken generally along line 4—4 of FIG. 1;

FIG. 5 is an exploded perspective view of a further embodiment of a disposable diaper embodying the principles of the present invention, which includes discrete regions of highly liquid-sorbent superabsorbent material;

FIG. 6 is a perspective view of the fibrous batt structure of the diaper shown in FIG. 5;

FIG. 7 is a cross-sectional view taken along lines 7—7 of FIG. 5 illustrating a preferred form of the fibrous batt absorbent structure of the present diaper;

FIG. 8 is a view similar to FIG. 7 illustrating a further embodiment of the fibrous batt absorbent structure of the present invention;

FIG. 9 is a diagrammatic view illustrating a method of manufacturing the present disposable diaper with superabsorbent material;

DESCRIPTION OF THE PREFERRED EMBODIMENT

Figure 10:
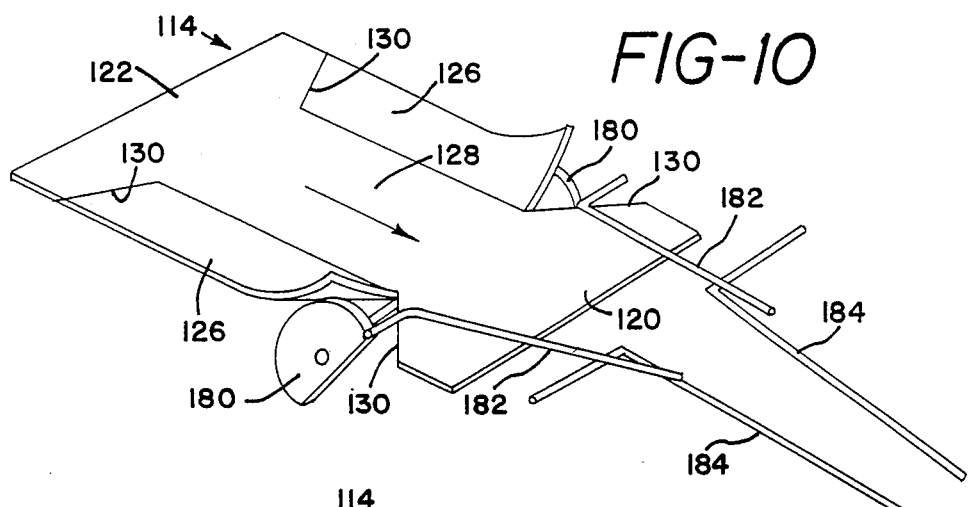
FIGS. 10–12 are diagrammatic views illustrating folding of flap sections of the fibrous batt structure of the present diaper during manufacture.

While this invention is susceptible of embodiment in many different forms, there is shown in the drawing and will herein be described in detail preferred and alternate embodiments, with the understanding that the present disclosure is to be considered as an exemplification of the principles of the invention and is not intended to limit the invention to the embodiments illustrated. The scope of the invention will be pointed out in the appended claims.

As used in the present disclosure, the term diaper is intended to refer to an absorbent article which is worn by an individual for absorbing urine and/or fecal matter. It is to be understood that diapers embodying the principles of the present invention can be appropriately sized for use by infants or babies, and can further be sized for use by incontinent adults. It will be further understood that absorbent articles other than disposable diapers can be provided with an absorbent unit or structure embodying the principles of the present invention.

Such articles can include sanitary napkins, tampons, incontinent pads, wound dressings, absorbent wipes, and the like.

Referring now to the drawings, the disposable diaper 10 of the present invention includes a facing layer 12 formed of a moisture pervious material, and adapted to be positioned adjacent to the infant's skin. Diaper 10 further includes a moisture impervious outer layer 16 substantially coextensive in external dimension with facing layer 12. Sandwiched between outer layers 12 and 16 is an absorbent unit 14 which is smaller in external dimension than outer layers 12 and 16, and which is disposed symmetrically with respect thereto. Absorbent unit 14 may be secured to backing sheet 16 by spaced, parallel glue lines, and layers 12 and 16 may be secured to one another outwardly of batt 14 by such glue lines, as is well understood by those skilled in the art.

Securement means is provided for releasably attaching the diaper 10 about the perineal area of the wearer, and such securement means may take the form of tape tabs 18 secured to backing sheet 16 at one end thereof, as is also well known to those skilled in the art.

As can be best seen in FIG. 1, batt 14 of the present invention is generally I-shaped. Batt 14 includes relatively wide end portions 20 and 22 connected by a relatively narrow central portion 24. Central portion 24 is adapted to be disposed in the crotch area of the wearer, and includes a plurality of thicknesses, or layers, to provide increased absorptive capacity in the crotch region. With reference to FIG. 2, central portion 24 includes a pair of side flap portions 26 at opposite sides of a medial portion 28. Side flap portions 26 are defined by lines of cutting 30 which extend inwardly from the side marginal edges of batt 14, and in the illustrated embodiment, batt 14 is initially a generally rectangular member, with cutting lines 30 being parallel to one another and to the end portions of the batt. Cutting lines 30 may be disposed at an angle with respect to one another and with respect to the side edges of the batt 14. Similarly, cutting lines 30 could be curved, if desired. Cutting lines 30 extend about $\frac{1}{3}$ of the width dimension of the batt 14, so that side flaps 26 and medial portion 28 have substantially the same dimension. As is evident by comparing FIGS. 2 and 4, batt 14 is given its I-shaped configuration by folding side flaps 26 inwardly into overlapping relationship with one another.

Several different types of facing materials may be used, for example, the facing may be a non-woven web made of a mixture of fibers consisting predominantly of inexpensive, short, cellulosic fibers such as short wood pulp fibers or cotton linters in amounts of 75 percent to 98 percent, the balance being textile length fibers such as rayon as described in U.S. Pat. No. 3,663,348 to Liloia, et al.

Non-woven facing materials suitable for use in disposable diapers of this invention can have fabric weights in the range of from about 0.5 to 5 ounces per square yard and densities of less than 0.15 g/cc., generally in the range of 0.05 to about 0.1 g/cc. The dry strength of the facing sheet for a fabric having a weight of about 1.5 ounces per square yard is at least 0.15 lbs. per inch of width in the machine direction and at least 0.1 lb. per inch of width in the cross direction. Such fabrics have good elongation, loft, softness, and drape characteristics. Facings may also be made of an apertured non-woven fabric which is formed, for example, in accordance with the teachings of U.S. Pat. Nos. 2,862,251; 3,081,514; and 3,081,515. Furthermore, facings may also be made from other types of fabric such as those disclosed and described in U.S. Pat. No. 3,485,706 to Evans. Such facings can be made of naturally occurring fibers, synthetic fibers or blends thereof. Typical facing sheets made of polyester type fibers may have a weight of about 0.75 ounces per square yard.

In addition, facings may be made from non-apertured materials such as non-woven isotropic webs or apertured polyolefin or polyester films having the desired moisture permeability. In all of the aforementioned facings, the materials should be relatively hydrophobic so as to retard wicking within the facing.

A suitable backing material for the disposable diapers embodying the present invention can be an opaque polyolefin; for example, polyethylene about 0.001 inch thick. Another suitable material for this purpose is polyethylene terephthalate having a thickness of about 0.005 inch.

The absorbent batt 14 preferably is formed of loosely compacted short cellulose fibers, such as wood pulp fibers, or cotton linters, or mixtures thereof, which primarily are held together by interfiber bonds requiring little or no added adhesive, as is known in the art. Briefly, these batts are a low bulk density coherent web of loosely compacted cellulose fibers, preferably comminuted wood pulp fibers, in the form of so-called "fluff."

The term "short fibers" as used herein, refers to fibers less than about $\frac{1}{4}$ inch in length, in contrast to "long fibers" or "textile length fibers" which are longer than about $\frac{1}{4}$ inch in length, and generally are between about $\frac{1}{2}$ and $2\frac{1}{2}$ inches in length.

The absorbent batt may also be formed of other vegetable fibers, such as bast fibers, including flax or linen, hemp, jute and ramie. Such bast fibers may be used alone, or in a mixture with wood pulp fibers or cotton linters.

Preferably the absorbent batt 14 includes a paper-like, densified compacted cellulosic fibrous layer 34 of relatively high wettability and relatively high fluid retentivity integral with the batt on the side thereof in contact with the backing sheet 16. The paper-like densified layer 34 is formed by slight moistening of one surface of the batt followed by the application of pressure thereto. This densified skin portion provides a wickability gradient to draw urine from the more loosely compacted cellulosic fibrous layer into the densified layer. The densified layer portion is described in more detail in Burgeni U.S. Pat. No. 3,017,304.

The composite density of the absorbent batt should be above about 0.07 gm/cc. and preferably between about 0.10 and 0.15 gm/cc. The foregoing density values are applicable to the diaper as produced. In storage and handling, the loft or thickness of the batt is increased to some extent, resulting in lower densities.

Densified layer 34 preferably includes regions of increased thickness dimension for adding strength to the batt 14 and providing a further wicking mechanism. The regions 36 of increased thickness dimension are illustrated (FIG. 4) as parallel longitudinally extending thickened densified lines. Such regions may be formed in accordance with the teachings of U.S. Pat. No. 3,938,522.

When the side flap sections 26 of a batt of the type described above are folded into overlapping relationship with one another, as is best seen in FIG. 4, a unique and highly advantageous batt structure is produced. In this regard, the central portion 24 of the batt includes a first densified layer 34a secured to backing sheet 16, a first loosely compacted layer 28a above layer 34a, a second loosely compacted layer 26a above layer 28a, a second densified layer 34b above layer 26a, a third loosely compacted layer 26b above densified layer 34b and a third densified layer 34c adjacent to, and in contact with, the undersurface of facing 12. Densified bridging portions 34d and 34e connect densified layers 34a and 34c, and 34a and 34b, respectively.

The densified layer 34 adds sufficient stiffness to the panel 14 to make it practical to form cutting lines 30 on a high speed production basis, and also provides sufficient integrity to the batt to enable the side flaps 26 to be folded into overlapping relationship with one another. The densified layers 34a, 34b and 34c, together with thickened lines 36 integral therewith, provide a wicking network for transmitting liquid rapidly toward unwetted remote portions of the batt. Bridging portions 34d and 34e provide a mechanism for directing liquid downwardly toward the lower portion of the batt 14. Loosely compacted layers 26a, 26b and 28a provide a reservoir for increased liquid storage capacity in the central or crotch region of the diaper.

In use, the disposable diaper is applied to the baby by laying out the diaper on a single flat surface and placing the baby thereon. The waist underlying end of the diaper is that end having the fastener means and the other end of the diaper extends downwardly between the baby's legs. Next, the downwardly extending edge of the diaper is brought up between the baby's legs to a position covering the perineum and contiguous with the front portion of the baby's waist. The diaper thereafter is secured to the baby by placing the corners of the waist portion of the abdomen covering end as far around the baby's waist as they will go and by bringing the corners of the underlying end of the diaper into an overlapping relationship with the aforementioned corners so that the diaper snugly encircles the baby's waist and provides a custom fit. The adhesive tape fasteners are then prepared for use and the diaper is secured in a desired position by simply urging the pressure-sensitive adhesive surface of the tape tab in contact with the adjacent outer surfaces of the opposite corner of the diaper.

With reference now to FIGS. 5-7, therein is disclosed a further embodiment of the present invention wherein highly-liquid sorbent superabsorbent material is incorporated in the fibrous batt structure of the diaper. In many respects, the disposable diaper of this embodiment, designated 110, is similar to the embodiment described above, and corresponding elements thereof are indicated by like reference numerals in the one-hundred series.

The disposable diaper 110 includes a facing sheet or layer 112 formed of a moisture pervious material which is adapted to be positioned adjacent to an infant's skin. Facing layer 112 may comprise fabrics, webs, or films having the desired moisture permeability, as described hereinabove. Preferably, the cover or facing provided on the absorbent structure of the present invention is a non-woven fabric having a high degree of moisture-permeability. For example, the fabric may be polyester, polyethylene, polypropylene, nylon, rayon or the like. Preferably, the fabric used for the cover is a lightweight fabric in the range of 0.3-5.0 oz. per square yard and with a density less than 0.2 gms/cc. The most suitable fabrics have unusually high elongation, loft, softness and drape characteristics. Though the cover is moisture-permeable, it is preferably of the type which after permeation of the moisture, prevents strike-back of the body fluid when the absorbent structure is approaching saturation. As also described above, the material from which facing layer 112 is formed is preferably relatively hydrophobic so as to retard and essentially prevent wicking of liquid within the facing layer.

The diaper 110 further includes a moisture impervious outer backing layer or sheet 116. Suitable cutout portions 112a and 116a defined by the facing layer 112 and the backing sheet 116, respectively, are preferably provided so as to define the crotch area of the diaper, thus permitting the diaper to conform to the torso of the wearer for a secure and comfortable fit.

Sandwiched between the facing layer 112 and the backing sheet 116 is an absorbent unit or structure 114 comprising a fibrous batt having discrete regions of highly liquid-sorbent superabsorbent material therein, as will be further described. The absorbent fibrous batt structure 114 may be secured to the backing sheet 116 by spaced, parallel glue lines, with the facing layer 112 and the backing sheet 116 secured to one another outwardly of the fibrous batt structure 114 by such glue lines, as is well understood by those skilled in the art.

As will be described, fibrous batt structure 114 is configured to absorb and retain liquid therein, and is further configured to preferably include a liquid-wicking mechanism or network to promote wicking of liquid within portions of the batt structure. In order to fully utilize the absorptive capacity of the fibrous batt structure and the superabsorbent material provided therein before any leakage from the diaper occurs, it is presently preferred to provide means for inhibiting leakage from the longitudinal ends of the diaper. In one form, such leakage inhibiting means can comprise a pair of moisture-impervious strips 117 provided at respective opposite ends of the batt structure between the batt structure and facing sheet 112, with the strips 117 acting to abate passage of liquid back through facing layer 112 from the ends of the batt structure. Strips 117 can comprise a polyolefin film such as employed for backing sheet 116 or a like substantially moisture-impervious film material. Strips 117 preferably extend 1-2 inches over the respective ends of batt structure 114, and are preferably dimensioned to extend beyond each lateral side of the batt structure.

In the preferred form, disposable diaper 110 is provided with suitable securement means for releasably attaching the diaper about the perineal area of a wearer, with such securement means illustrated in the form of tape tabs 118 secured to backing sheet 116 at one end thereof. Suitable elastic means 119 are further preferably provided on the backing sheet 116 at respective opposite sides of the crotch area, thus further enhancing the comfortable and secure fit of the diaper.

As shown in FIGS. 5 and 6, the absorbent fibrous batt structure 114 of disposable diaper 110 is preferably provided with a generally I-shaped configuration, while being formed from an initially generally rectangular member. To this end, the fibrous batt structure 114 includes opposite longitudinal end portions 120 and 122 connected by a relatively narrow central portion 124. The central portion 124 is adapted to be disposed in the crotch area of the wearer, and, as will be further described, includes a plurality of thicknesses, or layers, to provide increased absorptive capacity in the crotch region.

Central portion 124 preferably includes a pair of flap sections 126 provided at respective opposite sides of a medial section 128. Flap sections 126 are defined by lines of cutting 130 which extend inwardly from the side marginal edges of fibrous batt structure 114, and are preferably arranged so that each of the flap sections 126 is of a generally trapezoidal configuration. The cutting lines 130 preferably extend inwardly of the fibrous batt structure 114 a distance to provide each of the flap sections 126 with a width which is approximately equal to one-half the width of the medial section 128. Thus, when flap sections 126 are folded into overlapping relation with the medial section, the edges of the flap sections are positioned generally adjacent to each other along the longitudinal centerline of the batt structure.

Referring now particularly to FIG. 7, therein is illustrated a cross-sectional view of the medial section 128 of the fibrous batt structure 114 of the present diaper. The fibrous batt structure includes a first upper web 131 and a second lower web 133 each comprising highly porous, cellulosic fibrous material. The webs preferably comprise so-called short cellulose fibers, such as wood pulp fibers, or cotton linters, or mixtures thereof, which primarily are held together by interfiber bonds requiring little or no added adhesive, as described hereinabove, and are as known in the art. The batt may also be comprised of bast fibers, or mixtures of bast fibers and wood pulp fibers or cotton linters, as is described above.

The first upper web 131 and the second lower web 133 are superposed to define therebetween a web interface at which are positioned a plurality of spaced apart, longitudinally extending, parallel discrete regions of highly liquid-sorbent superabsorbent material, with such discrete regions of superabsorbent designated 135. Such superabsorbent material is capable of absorbing many times its own weight in liquid, and thus can greatly enhance the absorptive capacity of the fibrous batt structure 114.

The superabsorbent material present in the fibrous web is generally a water-insoluble but water-swellable polymeric substance capable of absorbing water in an amount that is at least 10 times the weight of the polymeric substance in its dry form. The superabsorbent material is in the form of particles which may be in the shape of fibers, spheres, bits of film, globules, or the like.

In one type of superabsorbent material, the particles or fibers may be described chemically as having a backbone of natural or synthetic polymers with hydrophilic groups or polymers containing hydrophilic groups being chemically bonded to the backbone or in intimate admixture therewith. Included in this class of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophilic. Such modified polymers may also be cross-linked to improve their water-insolubility.

These same polysaccharides may also serve, for example, as the backbone onto which other polymer moieties may be bonded by graft copolymerization techniques. Such grafted polysaccharides and their method of manufacture are described in U.S. Pat. No. 4,105,003 to Chatterjee et al. and may be described as polysaccharide chains having grafted thereon a hydrophilic chain of the general formula

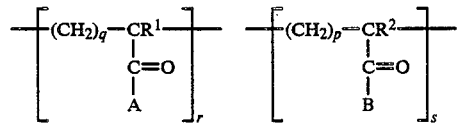

wherein A and B are selected from the group consisting of $-OR^3$, $-O$ (alkali metal), $-OHNH_3$, and $-NH_2$, wherein $R^1$, $R^2$ and $R^3$ are selected from the group consisting of hydrogen and alkyl having 1 to 4 or more carbon atoms, wherein r is an integer having a value of 0 to about 5000 or more, s is an integer having a value of 0 to about 5000 or more, r plus s is at least 500, p is an integer having a value of zero or 1 and q is an integer having a value of 1 to 4. The preferred hydrophilic chains are hydrolyzed polyacrylonitrile chains and copolymers of polyacrylamide and polysodium acrylate.

In addition to modified natural and regenerated polymers, the hydrocolloid particle component may comprise wholly synthetic hydrophilic particles. Examples of those now known in the art are polyacrylonitrile fibers which may be modified by grafting moieties thereon such as polyvinyl alcohol chains, polyvinyl alcohol itself, hydrophilic polyurethane, poly(alkyl phosphonates), partially hydrolyzed polyacrylamides (e.g., poly(N-N-dimethyl acrylamide), sulfonated polystyrene, or a class of poly-(alkylene oxide). These highly hydrophilic synthetic polymers may be modified by other chemical treatments such as cross-linking or hydrolysis. Further examples known in the art are the nonionic hydrophilic polymers such as polyoxyethylene, polyoxypropylene and mixtures thereof which have been suitably cross-linked, either chemically or by irradiation. Still another more recent type is derived of isobutylene-maleic anhydride copolymer.

In addition, naturally occurring materials such as gums, may be used. For instance, guar gum is suitable.

If the superabsorbent material is a powder it may be sprinkled onto the fibrous web either in dry form or the web may be moistened. If the superabsorbent is in granular form it may be desirable to slightly moisten the superabsorbent before placing it in contact with the web.

Any superabsorbent that absorbs large amounts of liquids is suitable for use in the absorbing layer of the present invention.

While many such superabsorbent materials tend to form a generally homogenous gelatinous mass upon wetting, other ones of such material tend to retain their particulate nature, at least to some extent, upon wetting, with the result being that such materials exhibit a "crumbly" texture when wetted. Use of this latter type of superabsorbent material is presently preferred, since it is believed that this resultant texture is less objectionable to users in the event that the superabsorbent becomes exposed during use or handling of the diaper. Further, such superabsorbent material forms a gel comprised of relatively rigid particles which have been found to exhibit relatively good liquid-retention when subjected to pressure, and which exhibit a relatively "dry" texture, when compared to superabsorbent materials which form a gelatinous mass when wetted. Additionally, superabsorbent material of this nature is believed to resist so-called "gel blocking" by the presence of interstitial voids within the wetted superabsorbent which permits liquid wicking within the material. One such superabsorbent material which has been successfully employed is commercially available under the name of Arakawa Arasorb 720, which is available from Arakawa Chemical USA, Inc., Chicago, Ill.

Characteristic physical properties of the Arakawa Arasorb 720 material as reported by the manufacturer are as follows:

| Distribution of Particle Size | |
|---|---|
| Over 20 mesh | 1.8% |
| 20–145 mesh | 81.8 |
| Less than 145 mesh | 16.4 |
| Bulk Specific Gravity (grams/cc) | |
| Rough state | 0.57 |
| Rigid state | 0.69 |
| Water content (percent) | 15.6 |
| Absorbency (grams of liquid per gram of material) | |
| Deionized water | 335 |
| Physiological Saline Solution | 48 |
| Urine | 39 |
| Absorbing Speed (seconds) | 2.9 |
| Rigidity of gel (dyne/cm$^2$) | $4.47 \times 10^4$ |

It is believed that the Arakawa Arasorb 720 material is formulated in accordance with the teachings of Japanese Patent Disclosure No. 84-80459.

Of course, a wide variety of superabsorbent materials can be employed in a disposable diaper construction embodying the principles of the present invention. However, it is preferred that the superabsorbent which is employed not act to reduce the surface tension of liquid in the batt structure.

As noted hereinabove, most highly liquid-sorbent superabsorbent materials generally do not promote good liquid wicking or transport within an absorbent structure, despite the high absorbent capacity of such materials. Additionally, such materials can be relatively slow in absorbing liquid (as compared to a pulp fiber batt, for example).

In view of this, effective use of superabsorbent material in a disposable diaper calls for the provision of an intimately associated liquid-wicking structure or network to promote wicking or transport of liquid to various portions of the absorbent structure from an initially wetted area, as well as the provision of an intimately associated liquid "reservoir" (such as an absorbent fibrous structure) to retain the liquid until it is absorbed by the superabsorbent material. Good liquid wicking is particularly important in an absorbent article comprising a disposable diaper in view of the substantial volume of liquid which must be absorbed, and the relatively brief period during which such liquid is introduced. Without effective liquid-wicking, the enhanced absorptive capacity provided by the superabsorbent material is not optimally utilized. Without associated absorptive capacity, such as in the form of an absorbent fibrous matrix structure, the liquid is not prevented from leaking as the superabsorbent performs its absorption function.

Accordingly, the medial section of 128 of fibrous batt structure 114 is provided with a plurality of relatively densified compacted embossments 137 provided on respective opposite sides of each longitudinally extending superabsorbent region 135 and between adjacent ones of the regions 135. Embossments 137 are formed by densifying and compacting the first and second fibrous webs 131 and 133, as will be further described hereinafter. Thus, a plurality of the embossments 137 are preferably provided in longitudinally extending, spaced parallel relation at areas of the fibrous batt structure which are relatively free of superabsorbent material. Because the superabsorbent material can act to abate wicking of liquid through the relatively small capillaries of the densified embossments 137, it is preferred that the embossments be as free of superabsorbent as is practicable. However, the particulate nature of the unwetted superabsorbent can make it difficult to confine the superabsorbent within the discrete regions 135 during manufacture, and thus it will be appreciated that the embossments 137 are preferably substantially free of superabsorbent, but not necessarily completely free of such material.

The densified embossments 137 are provided adjacent to the discrete regions 135 of superabsorbent in the sense that the embossments can be in contact with the superabsorbent material, or in closely spaced relation thereto, depending upon the width of the embossments, the width of the regions 135 of superabsorbent material, and the quantity of superabsorbent material. Thus, the embossments 137 are provided in intimate operative association with the superabsorbent material for promoting liquid transport to all of the superabsorbent.

The densified wicking embossments 137 not only provide a highly effective wicking mechanism in intimate association with the discrete regions of superabsorbent material 135, but further act to separate the regions of superabsorbent from each other, lend desired stability and structural integrity to the fibrous batt structure 114, and provide desirable absorptive capacity together with the associated relatively uncompacted portions of webs 131 and 133 for holding liquid until it is absorbed by the superabsorbent. In order to further contain the superabsorbent material in position within the fibrous batt, a pair of transverse embossments 139 can be provided which extend along respective opposite longitudinal ends of the parallel embossments 137. By this construction, each discrete region 135 of superabsorbent material is bounded and surrounded by embossments formed between the first and second fibrous webs 131 and 133.

It is presently contemplated that as much superabsorbent be employed as is possible, relative to the amount of fibrous batt material, while still maintaining the stability and integrity of the batt structure. Superabsorbent can be employed in a weight ratio of at least approximately 5 percent to approximately 70 percent, weight of superabsorbent to weight of fibrous batt material, and more preferably in a weight ratio of about 10–50 percent.

By way of example, it is presently contemplated that four discrete regions 135 of superabsorbent be provided extending longitudinally of medial section 128 of the batt structure 114. In a disposable baby diaper having an overall length of about 17.5 inches, and an absorbent batt structure 114 approximately 15 inches in length, embossments 137 are preferably formed to be approximately 13 inches in length, with each discrete region 135 of superabsorbent material being approximately 11 inches in length. Embossments 137 are preferably spaced approximately 1.0 to 1.125 inches apart. The width of the discrete regions 135 themselves is selected to be as wide as possible while avoiding deposition of the superabsorbent particles in the wicking embossments. The lateral-most ones of embossments 137 are preferably spaced approximately 0.75 inches from the respective fold lines for flap sections 126.

While it is possible to form an absorbent structure in accordance with the teachings herein having a plurality of elongated discrete regions of superabsorbent material wherein the regions differ in length and/or comprise differing quantities of superabsorbent, it is presently contemplated that regions 135 be of substantially equal lengths and each include substantially equal quantities of superabsorbent material.

It can also be desirable to provide discrete regions of superabsorbent material within the flap sections 126 of the fibrous batt structure, as shown in phantom line at 135' in FIG. 5. If such regions are provided in the flap sections, its preferred that they be bounded by densified embossments formed in the first and second webs 131 and 133, as further illustrated in FIG. 5 at 137'.

In the preferred form of the present invention, the absorbent batt structure 114 is provided with at least one relatively densified and compacted liquid-wicking layer formed integrally with one of the first and second webs 131 and 133. Such a wicking layer is paper-like in nature, and is provided such that it extends throughout at least medial section 128 of the fibrous batt 114. To facilitate cutting and folding of the flap sections 126 of the fibrous batt structure 114, it is preferred that the densified compacted wicking layer be provided throughout the width of the batt structure.

It is presently preferred that the above-described densified compacted wicking layer be provided in intimate association with the discrete regions 135 of superabsorbent material, and thus, as illustrated in FIG. 7, is provided at the inner surface of one of the fibrous webs 131 and 133 at the interface therebetween, preferably at the inner surface of first upper web 131. Provision of this densified layer at the web interface desirably acts to "fix" and stabilize the particulate superabsorbent. Such stabilization of the particulate material is believed to result from moistening of at least some of the particles attendant to formation of densified wicking layer 141 by moistening of upper web 131, thereby resulting in the moistened particles adhering to the fibers of the wicking layer. Further, at least some of the superabsorbent particles are believed to become mechanically trapped and locked in place since the superabsorbent material extends into and is integrated with, to some extent, the fibrous matrix of batt structure 114. This mechanical trapping and locking and integration of the superabsorbent into the fiber matrix is enhanced by virtue of application of pressure and compaction attendant to formation of wicking layer 141. The stabilization of the superabsorbent material provided by the present construction desirably acts to prevent migration and movement of the particulate superabsorbent, which can otherwise occur attendant to manufacture, packaging, storage and shipment of articles having particulate superabsorbent material therein.

As will be further described, the paper-like densified wicking layer 141 is formed by slight moistening of the surface of the fibrous web 131 followed by application of pressure thereto. The integrally formed densified wicking layer thus provides a wickability gradiant to draw urine and other fluid from the more loosely compacted cellulosic fibrous web material into the densified layer. The formation and characteristics of the densified wicking layer 141 are described more in detail in Burgeni U.S. Pat. No. 3,017,304.

While the densified wicking layer 141 is illustrated as positioned above the discrete regions 135 of superabsorbent material, it is believed that application of relatively high pressure during formation of the layer 141 can result in some moisture reaching the upper surface of lower web 133, and thereby result in the formation of another densified paper-like wicking layer integral with the upper surface of web 133. Thus, it is within the purview of the present invention to form each of the upper and lower webs with an integral wicking layer at the web interface (note the provision of a densified layer on web 133 shown in phantom line in FIG. 7 at 141'), with the regions 135 of superabsorbent material thereby disposed between the two densified wicking layers. If the formation of two such wicking layers at the web interface is to be provided, application of moisture (such as by a water spray) to the upper surface of web 133 prior to deposition of superabsorbent material thereon can be effected, in addition to the application of moisture to web 131 for formation of wicking layer 141. In an instance where moisture is applied to only one of the fibrous webs and is to be transferred during compaction to the other of the webs for forming each web with an integral densified layer, it will be understood that the densified layer formed on the web to which moisture is applied will be heavier and thicker than the other densified layer which is formed.

The densified wicking layer 141 not only promotes wicking or transport of liquid to various portions of the absorbent fibrous batt structure, but further lends desired stability and structural integrity to the structure. In this regard, the densified wicking layer 141 acts to abate and prevent splitting or other degradation of the fibrous batt attendant to swelling of the wetted superabsorbent material. In order to further abate such splitting of the fibrous batt, the upper surface of the batt structure can be provided with another densified compacted integrally formed wicking layer, designated 143, which is illustrated as being formed on the outer surface of first upper web 131. While the formation of densified layers 141 and 143 desirably provides enhanced integrity and stability for the fibrous batt structure, it can be desirable to further enhance the stability by the provision of a paper tissue sheet layer above the discrete regions of superabsorbent material at the interface between webs 131 and 133, above the medial section 128 (and below flap sections 126) of the batt structure 114, or above the entire batt structure beneath facing sheet 112. When such a paper tissue sheet layer is provided at the web interface adjacent the superabsorbent material and a densified wicking layer such as 141, it is believed that the tissue layer becomes integrated with the densified wicking layer, thus further desirably enhancing the stability and integrity of the absorbent structure.

Before describing the method of manufacturing the present diaper construction, an alternate configuration for absorbent batt structure 114 will be described, as illustrated in FIG. 8. FIG. 8 illustrates a cross-sectional configuration of the medial section 228 of a fibrous batt structure generally as described above. The batt structure includes first and second upper and lower webs 231 and 233 which are superposed to define a web interface therebetween. Discrete spaced apart regions of superabsorbent material 235 are provided at the web interface, preferably in the form of elongated longitudinally extending deposits of superabsorbent material. As in the previously described embodiment, parallel, longitudinally extending densified embossments 237 are formed between the upper and lower webs 231 and 233 for lending stability to the batt structure while providing a wicking mechanism in intimate association with the deposits of superabsorbent material. In the illustrated embodiment, an optionally provided integral densified compacted wicking layer 241 is shown on the outer surfaces of one of the webs 231 and 233, i.e., on the outer surface of lower web 233.

Referring now to FIG. 9, the method of manufacturing the disposable diaper 110 illustrated in FIGS. 5-7 will be described. In many respects, conventional and known forming techniques can desirably be employed for efficient and economical formation of a disposable diaper having superabsorbent material embodying the principles of the present invention.

Manufacture of the present diaper is initiated by formation of the first upper and second lower fibrous webs 131 and 133 as elongated continuous webs which are subsequently joined and later severed into individual fibrous batt structures. To this end, FIG. 9 shows the provision of two rolls 150 of compacted fibrous material such as comprising comminuted wood pulp, with the rolls supplying respective Fitzmills 152. The mills 152 defiberize the fibrous material into individual short fibers, with each mill providing a stream of fibers which is blown onto a respective forming belt 154 in a known and conventional manner. Respective compacting rolls 156 compress the air blown layer of fibers into respective continuous upper and lower fibrous webs 131 and 133. It is presently preferred that upper web 131 be formed so that it is of a relatively heavier weight than lower web 133, thus desirably acting to confine and retain the subsequently-deposited superabsorbent material in the batt structure being formed, thus lending desired stability and structural integrity to the batt structure. For example, upper web 131 can be formed to be approximately 30-40 percent heavier than lower web 133.

Particularly referring to the continuous upper web 131 thus formed, the web can be guided through the nip of suitable guide rollers 158, and thereafter be moistened with a suitable water spray at 160 for formation of integral densified wicking layer 141. The web 131 can also be moistened at its opposite surface by a suitable water spray at 162 if the web is to be formed with an integral outer densified layer 143. The now moistened web 13 is suitably guided to a pair of combining rollers 164 whereat the web is superposed with the continuous lower web 133. If the densified layers are not intended to be formed throughout the surfaces of the web 131, suitably confined water sprays can be employed to limit the extent of the densified layers. It is presently contemplated that the densified wicking layer 141 be formed to extend the same length of each batt structure as the densified embossments 137.

Referring now to the formation of second lower web 133, the web can be directed from its forming belt 154 through a suitable pair of guide rollers 166, and thereafter fed through the nip of a pair of light compaction rollers 168. The compaction rollers 168 preferably effect a light compaction of the lower web 133 to thereby abate the tendency of subsequently deposited particulate superabsorbent material to "sift" through the web when deposited thereon. In order to facilitate deposition of the superabsorbent material in discrete regions 135 of the fibrous batt structure, the compaction rollers 168 preferably are configured to form dished or recessed channel areas within a medial portion of the lower fibrous web 133 so that the superabsorbent material can be deposited within the channels thus formed, thereby tending to confine the particulate superabsorbent and provide regions between the adjacent elongated deposits which are relatively and preferably substantially free of the superabsorbent material.

Deposition of the particulate superabsorbent on the lower web 133 is effected by a suitable indexable dispensing means 170. Dispensing means 170 is indexable so that the elongated discrete regions of superabsorbent material can be provided to extend the length of the medial section of the fibrous batt 114 being formed, without extending through the end portions 120 and 122 thereof.

The lower fibrous web 133 is fed and directed into the nip of combining rollers 164 in superposed relation beneath the upper web 131 to thus form a continuous fibrous batt which will subsequently be configured into a series of the fibrous batt structures 114 arranged in continuous, end-to-end relation.

After the first and second webs 131 and 133 have been superposed at rollers 164, the webs are passed between suitable embossment forming means, illustrated as comprising embossing rollers 172. Embossing rollers 172 compress, calender and densify the upper and lower webs 131 and 133 so as to form the parallel longitudinal densified embossments 137 of the absorbent batt structure. Since the embossments 137 preferably do not extend the entire length of the batt structure 114, embossing rollers 172 are suitably configured for periodic embossment, such as by providing one or both of the rollers with suitable non-compacting "flats", or by providing suitable mechanical means for periodically moving the embossing rollers 172 into and out of engagement with the continuous fibrous batt. The rollers 172 can be configured to likewise form the transverse embossments 139, or such transverse embossments can be formed with an additional set of embossing rollers.

The now-embossed continuous fibrous batt is next fed and guided between a pair of calendering or compacting rollers 174 which apply pressure to the web structure for formation of integral densified layer 141 in spaced relation to the upper surface of the fibrous batt, and densified layer 143, owing to the presence of moisture previously applied to the continuous upper web 133. The pressure applied by the rollers 174 may vary from about 5 to about 100 or more pounds per square inch, with the commercially preferable range being from about 10 to about 50 pounds per square inch.

It is presently contemplated that the fibrous webs 131 and 133, inclusive of one or more integral densified layers formed therewith, exhibit a composite density in the range of approximately 0.07 to approximately 0.50 grams/cc, exclusive of superabsorbent material provided in the fibrous structure.

Figure 11:
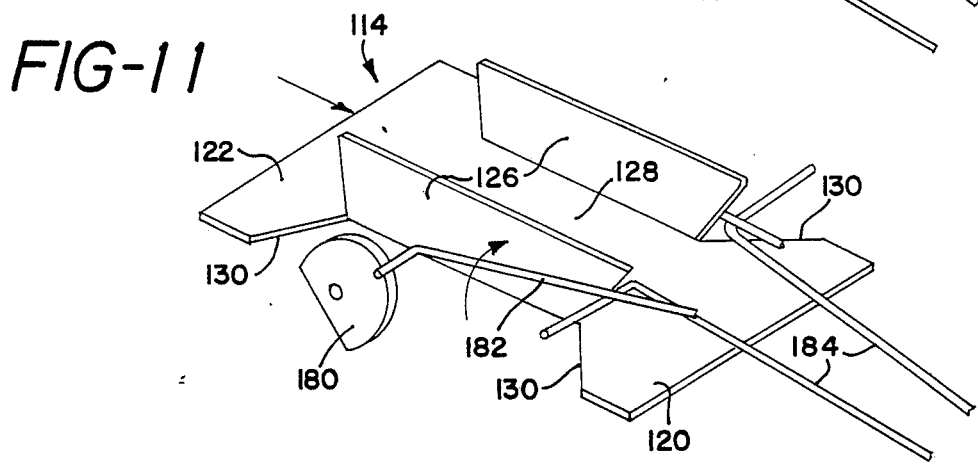
Figure 12:
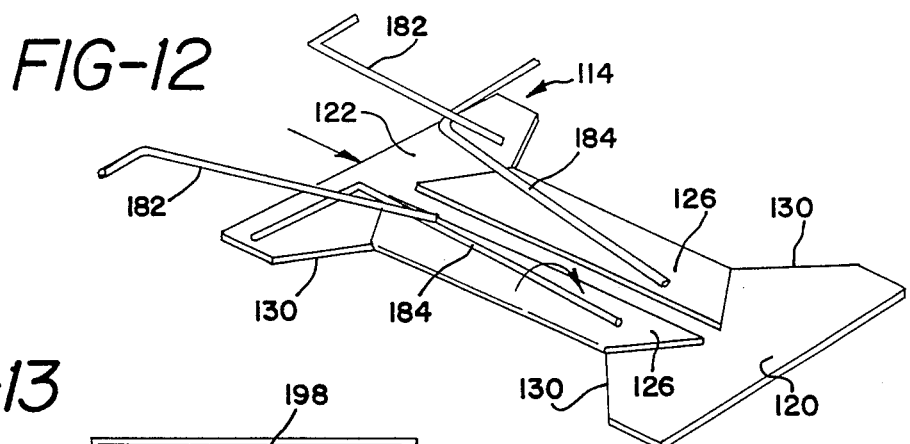

After formation of the integral densified compacted layers in the batt structure, the continuous batt is passed through cooperating cutting rollers 176 for formation of cutting lines 130 which define the flap sections 126 of the fibrous batt structure being formed. The continuous fibrous batt is next guided through a folding station, generally designated 178, where folding of the flap sections 126 is effected generally in accordance with the diagrammatic illustration shown in FIGS. 10-12. These figures show a single one of the end-to-end fibrous batt structures 114, with the batt structures being advanced through the folding station in the direction indicated by the arrows in FIGS. 10-12. During advancement in this manner, the side flap sections 126 are urged upwardly by suitable rotating elements 180, with the flap sections subsequently folded into overlapping relation with the medial section of the batt structure by suitable guide rails 182 and 184. After folding, the continuous fibrous batt structure is cut by a suitable cutting mechanism 185 into individual ones of the fibrous batt structures 114.

After cutting of the individual fibrous batt structures, the batt structures are sandwiched between the upper facing layer 112 and the lower backing sheet 116 to complete formation of the diaper 110. To this end, a roll 186 of facing layer material is provided, with a continuous length of the facing layer material 112 guided into superposed relation with the individual batt structures 114 between a pair of combining rollers 187. Similarly, a roll 188 of the backing sheet material provides a continuous length of backing layer 116, with suitable adhesive dispensing means 189 provided for applying adhesive to the backing sheet for subsequent adherence of each fibrous batt structure 116 and the respective facing layer 112 thereto.

The provision of moisture-impervious strips 117 at opposite ends of each batt structure 114 can be effected at this stage of the manufacturing process. By way of illustration, a roll of moisture-impervious material 190 can be provided for this purpose, with a suitable cutting mechanism 191 employed for forming strips 117' of the moisture-impervious material. These strips 117' can be subsequently suitably adhered to facing layer material 112 at spaced apart intervals such as by heat-sealing at heat-sealing rollers 192. If the facing layer material 112 and the strips 117' are not heat-sealable or not readily heat-sealable, the strips 117' can be adhered to the facing material by suitable adhesive means.

Each strip 117' is thus positioned to "span" and extend between adjacent ones of the now-severed batt structures 114 as the facing layer material 119 is fed between combining rollers 187. During subsequent cutting of the end-to-end diaper constructions, each strip 117' thus provides the moisture-impervious strip 117 at the "trailing" end of one diaper, and the strip 117 at the "leading" end of the next-following diaper.

Application of elastic means 119 to backing sheet 116 can also be effected generally at combining rolls 187. Application of the elastic material can be effected in accordance with well-known, conventional techniques, such as in accordance with the teachings of U.S. Pat. No. 4,081,301, to Buell. Generally, this step of the present method entails providing rolls 195 of elastic material 119, with the number of rolls of elastic material corresponding to the number of elastic elements to be applied to the backing sheet 116 of each diaper 110. The elastic material is guided through a tensioning mechanism 196 which stretches the material, with a suitable adhesive-applying means 197 provided for applying adhesive to the tensioned elastic material. The elastic material is fed between the rollers 187 and adhered by the backing sheet 116 of each diaper being formed. The elastic material is maintained in a tensioned condition until the individual diapers 110 are severed from the continuous end-to-end configuration in which they are formed.

Figure 13:
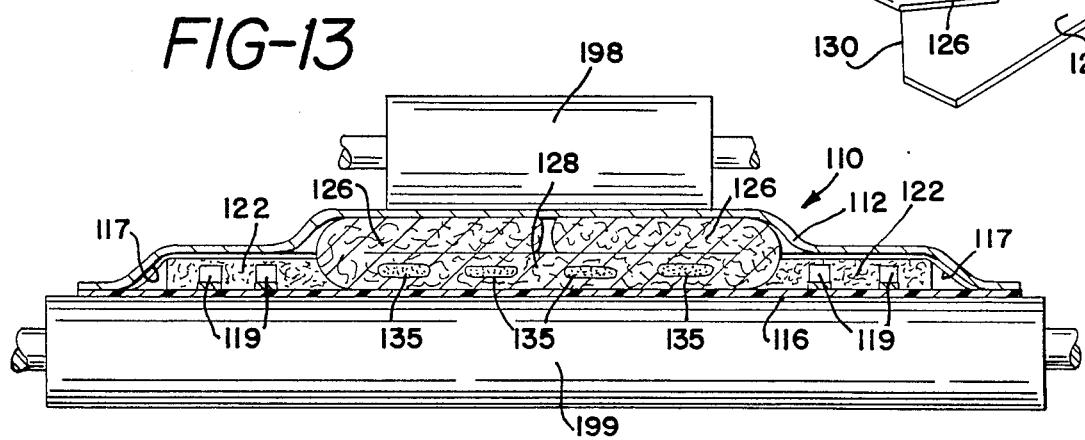
FIG. 13 is a view taken along lines 13—13 of FIG. 9 further illustrating manufacture of the present disposable diaper.

Advancement of the diapers being formed through the manufacturing line is at least in part effected via tensioning or pull rollers 198 and 199. Significantly, it has been found that an improved product is obtained by avoiding compression and compaction of the fold lines about which the flap sections 126 of the fibrous batt structure are folded. Accordingly, and as best illustrated in FIG. 13, the upper tensioning roller 198 is dimensioned so as to exert pressure on the now completed diaper inwardly of the fold lines for the flap sections 126. Thus, the fold lines for the flap sections are substantially uncompressed and uncompacted, thereby avoiding densification of the fibrous batt material at the fold lines which can otherwise act to wick liquid into the fold lines, which can result in leakage of the diaper product at the sides thereof.

Completion of diaper manufacture is effected at cutting mechanism 200 whereat the individual diapers 110 are severed from each other. The diapers can now be advanced to suitable folding and packaging mechanisms for subsequent packaging storage and shipment.

From the foregoing, it will be observed that numerous modifications and variations can be effected without departing from the true spirit and scope of the novel concept of the present invention. It will be understood that no limitation with respect to the specific embodiments illustrated herein is intended or should be inferred. It is, of course, intended to cover by the appended claims all such modifications as fall within the scope of the claims.

What is claimed is:

1. A method of manufacturing a disposable diaper, comprising the steps of:
    forming first and second fibrous webs of highly porous cellulosic fibrous material;
    depositing a quantity of highly liquid-sorbent superabsorbent material on said second fibrous web on at least a medial section thereof to provide a plurality of spaced apart discrete regions of superabsorbent material;
    positioning facing surfaces of said first and second fibrous webs in superposed relation to define a web interface therebetween at which said discrete regions of superabsorbent material are provided to thereby form a fibrous batt having a medial section corresponding to the medial section of said second fibrous web;
    joining said first and second fibrous webs to each other, including forming a plurality of densified compacted wicking embossments between and adjacent to, but spaced from, said discrete regions of superabsorbent material to promote wicking of liquid, said joining step being performed so that said densified embossments comprise integrated fibrous material of said first and second fibrous webs for joining said webs to each other to integrate said fibrous webs for stabilizing said fibrous batt formed therefrom; and
    providing a first outer backing sheet and a second moisture-pervious facing sheet on respective opposite sides of said fibrous batt in superposed relation therewith.

2. A method of manufacturing a disposable diaper as set forth in claim 1, including
    providing a densified compacted wicking layer integrated with at least one o: said first and second fibrous webs.

3. A method of manufacturing a disposable diaper as set forth in claim 2, including
    providing said densified compacted wicking layer at said web interface of said fibrous batt.

4. A method of manufacturing a disposable diaper as set forth in claim 1, including
    cutting said fibrous batt to form a pair of flap sections at respective opposite sides of said medial section of said batt, and folding said flap sections at respective fold lines into overlapping relationship with said medial batt section.

5. A method of manufacturing a disposable diaper as set forth in claim 4, including
providing a densified compacted wicking layer integrated with at least one of said first and second fibrous webs.

6. A method of manufacturing a disposable diaper as set forth in claim 5, including
providing said densified wicking layer at said web interface.

7. A method of manufacturing a disposable diaper as set forth in claim 3, including
providing said densified wicking layer on said first upper web at said web interface, and providing another densified compacted wicking layer on the opposite outer surface of said first upper web.

8. A method of manufacturing a disposable diaper as set forth in claim 1, including
depositing said superabsorbent material on said second fibrous web to provide a plurality of said discrete regions extending longitudinally of said fibrous batt in spaced apart parallel relation, and forming said densified compacted wicking embossments in longitudinally extending spaced apart parallel relation on respective opposite sides of each said discrete region of superabsorbent material.

9. A method of manufacturing a disposable diaper as set forth in claim 4, including
forming a plurality of said diapers in continuous end-to-end relation, and severing said diapers from each other, including advancing said continuous plurality of diapers with tensioning pull roller means configured to avoid compaction of said fold lines of said flap sections of the fibrous batt of each said diaper.

10. A method of forming an absorbent unit for use in an absorbent article, comprising the steps of:
forming first and second fibrous webs of highly porous cellulosic fibrous material;
depositing a quantity of highly liquid-sorbent superabsorbent material on said second fibrous web on at least a medial section thereof to provide a plurality of spaced apart discrete regions of superabsorbent material and to define relatively superabsorbent-free areas;
positioning facing surfaces of said first and second fibrous webs in superposed relation to define a web interface therebetween at which said discrete regions of superabsorbent material are provided to thereby form a fibrous batt having a medial section corresponding to the medial section of said second fibrous web;
joining said first and second fibrous webs to each other, including forming relatively densified, liquid-wicking embossments in said first and second fibrous webs at said superabsorbent-free areas adjacent said discrete superabsorbent regions to promote wicking of liquid along the relatively densified embossments; and
providing at least one of said first and second fibrous webs with an integrated, relatively densified paper-like liquid wicking layer at the surface thereof at said web interface, said providing step being performed so that the embossments on said at least one fibrous web are joined to said wicking layer for further promoting wicking of liquid along the relatively densified wicking layer, at least a portion of said wicking layer being in physical contact with at least a portion of said superabsorbent material to promote liquid transfer therebetween.

11. A method of forming an absorbent unit in accordance with claim 10, including
providing each of said first and second fibrous webs with an integrated, relatively-densified paper-like wicking layer at said web interface.

12. A method of forming an absorbent unit in accordance with claim 10, including
forming said relatively densified, liquid-wicking embossments to bound each said discrete region of superabsorbent material.

13. A method of forming an absorbent unit in accordance with claim 10, including
providing said densified wicking layer on said first upper web at said web interface, and forming said batt with another paper-like, densified fibrous wicking layer at the upper surface of said first upper web.

14. A method of forming an absorbent unit in accordance with claim 10, including
depositing said superabsorbent material to form said discrete regions to extend longitudinally of said fibrous batt, and forming said liquid-wicking embossments to extend longitudinally of said fibrous batt in spaced parallel relation to each other between and on respective opposite sides of said discrete regions of superabsorbent material.

15. A method of forming an absorbent unit in accordance with claim 14, including
providing a first outer backing sheet and a second moisture-pervious facing sheet on respective opposite sides of said fibrous batt in superposed relation therewith to form a disposable diaper.

16. A method of forming an absorbent unit for use in an absorbent article, comprising the steps of:
forming first and second fibrous webs of highly porous cellulosic fibrous material;
depositing a quantity of highly liquid-sorbent superabsorbent material on said second fibrous web on at least a medial section thereof to provide a plurality of spaced apart discrete regions of superabsorbent material and to define relatively superabsorbent-free areas;
positioning facing surfaces of said first and second fibrous webs in superposed relation to define a web interface therebetween at which said discrete regions of superabsorbent material are provided to thereby form a fibrous batt having a medial section corresponding to the medial section of said second fibrous web; and
joining said first and second fibrous webs to each other, including forming relatively densified liquid-wicking embossments in said first and second fibrous webs at said superabsorbent-free areas adjacent to but spaced from said discrete superabsorbent regions to promote wicking of liquid, said joining step being performed so that said densified embossments comprise integrated fibrous material of said first and second webs for joining said webs to each other for integrating and stabilizing said absorbent unit.

17. A method of forming an absorbent unit in accordance with claim 16, including forming at least one of said first and second webs with an integrally formed, paper-like, densified compacted cellulosic fibrous wicking layer to further promote wicking of liquid.

18. A method of forming an absorbent unit in accordance with claim 17, including
depositing said superabsorbent material to form said discrete regions to extend longitudinally of said fibrous batt, and forming said liquid-wicking embossments to extend longitudinally of said fibrous batt in spaced parallel relation to each other between and on respective opposite sides of said discrete regions of superabsorbent material.

19. A method of forming an absorbent unit in accordance with claim 16, including
forming said relatively densified, liquid-wicking embossments to bound each said discrete region of superabsorbent material.

20. A method of forming an absorbent unit in accordance with claim 16, including
providing a first outer backing sheet and a second moisture-pervious facing sheet on respective opposite sides of said fibrous batt in superposed relation therewith to form a disposable diaper.

21. A method of forming an absorbent unit for use in an absorbent article, comprising the steps of:
forming first and second fibrous webs of highly porous cellulosic fibrous material;
depositing a quantity of highly liquid-sorbent superabsorbent material on said second fibrous web on at least a medial section thereof to provide a plurality of spaced apart discrete regions of superabsorbent material;
positioning facing surfaces of said first and second fibrous webs in superposed relation to define a web interface therebetween at which said discrete regions of superabsorbent material are provided to thereby form a fibrous batt having a medial section corresponding to the medial section of said second fibrous web;
joining said first and second fibrous webs to each other; and
providing at least one of said first and second fibrous webs with an integrally formed, relatively densified, paper-like wicking layer at the surface thereof at said web interface for promoting wicking and transport of liquid along said relatively densified wicking layer from a region of introduction of liquid into said absorbent unit, at least a portion of said wicking layer being in physical contact with at least a portion of said superabsorbent material to promote liquid transfer therebetween.

22. A method of forming an absorbent unit in accordance with claim 21, including
depositing said superabsorbent material to form said discrete regions to extend longitudinally of said fibrous batt.

23. A method of forming an absorbent unit in accordance with claim 21, including
forming relatively densified, liquid-wicking embossments in said first and second webs so that said discrete regions of superabsorbent material are bonded by said liquid-wicking embossments.

24. A method of forming an absorbent unit in accordance with claim 21, including
providing each said first and second fibrous webs with an integrally formed, relatively densified, paper-like wicking layer at the surface thereof at said web interface.

25. A method of forming an absorbent unit in accordance with claim 21, including
providing a first outer backing sheet and a second moisture-pervious facing sheet on respective opposite sides of said fibrous batt in superposed relation therewith to form a disposable diaper.

26. A method of forming an absorbent unit in accordance with claim 25, wherein
said first outer backing sheet is provided in the form of a moisture-impervious backing sheet.

* * * * *